United States Patent
Hateley et al.

(10) Patent No.: US 7,572,937 B2
(45) Date of Patent: *Aug. 11, 2009

(54) PROCESS FOR PREPARING AMINO ACIDS USING AMIDOCARBONYLATION REACTION

(75) Inventors: Martin Hateley, Aschaffenburg (DE); Thomas Hauhlner, Bad Orb (DE); Christoph Weckbecker, Gründau (DE); Klaus Huthmacher, Gelnhausen (DE); Dieter Buss, Aschaffenburg (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/570,319

(22) PCT Filed: May 14, 2005

(86) PCT No.: PCT/EP2005/005295

§ 371 (c)(1),
(2), (4) Date: Dec. 8, 2006

(87) PCT Pub. No.: WO2005/121079

PCT Pub. Date: Dec. 22, 2005

(65) Prior Publication Data

US 2007/0244339 A1 Oct. 18, 2007

(30) Foreign Application Priority Data

Jun. 11, 2004 (GB) .................................. 0413092.8

(51) Int. Cl.
*C07C 319/12* (2006.01)
*C07C 227/20* (2006.01)
(52) U.S. Cl. .................. 562/559; 562/557; 562/575
(58) Field of Classification Search .............. 562/557, 562/559, 575
See application file for complete search history.

(56) References Cited

U.S. PATENT DOCUMENTS

| | | | | |
|---|---|---|---|---|
| 3,236,597 A | * | 2/1966 | Knap | 423/417 |
| 3,725,534 A | * | 4/1973 | Reisch | 423/417 |
| 3,766,266 A | * | 10/1973 | Wakamatsu et al. | 562/518 |
| 3,816,337 A | * | 6/1974 | Usami et al. | 502/30 |
| 3,855,396 A | * | 12/1974 | Kniese et al. | 423/417 |
| 5,097,065 A | * | 3/1992 | Lin | 562/450 |
| 5,650,537 A | * | 7/1997 | Beller et al. | 562/519 |
| 5,756,413 A | * | 5/1998 | Bogdanovic et al. | 502/24 |
| 5,858,993 A | * | 1/1999 | Pickart | 514/60 |
| 5,972,999 A | * | 10/1999 | Murad | 514/474 |
| 6,130,351 A | * | 10/2000 | Stern et al. | 562/17 |
| 6,162,753 A | * | 12/2000 | Geissler et al. | 502/24 |
| 6,979,468 B1 | * | 12/2005 | Pollard | 424/643 |
| 2007/0184017 A1 | * | 8/2007 | Faryniarz et al. | 424/78.37 |
| 2007/0203354 A1 | * | 8/2007 | Ramirez et al. | 556/114 |
| 2007/0244339 A1 | * | 10/2007 | Hateley et al. | 562/406 |

FOREIGN PATENT DOCUMENTS

| | | |
|---|---|---|
| EP | 0 281 707 A | 9/1988 |
| EP | 779102 A1 * | 6/1997 |
| EP | 0 919 539 A | 6/1999 |
| FR | 2 591 221 | 6/1987 |
| JP | 62158239 A * | 7/1987 |

OTHER PUBLICATIONS

International Search Report, Oct. 27, 2005.

* cited by examiner

*Primary Examiner*—Peter G O'Sullivan
(74) *Attorney, Agent, or Firm*—Pillsbury Winthrop Shaw Pittman LLP

(57) ABSTRACT

The present invention relates to a sequence for the preparation of amino acids, for example alpha amino acids, in particular methionine, by making use of an amidocarbonylation reaction and reuse of the catalyst.

12 Claims, 1 Drawing Sheet

PROCESS FOR PREPARING AMINO ACIDS USING AMIDOCARBONYLATION REACTION

Figure 1:
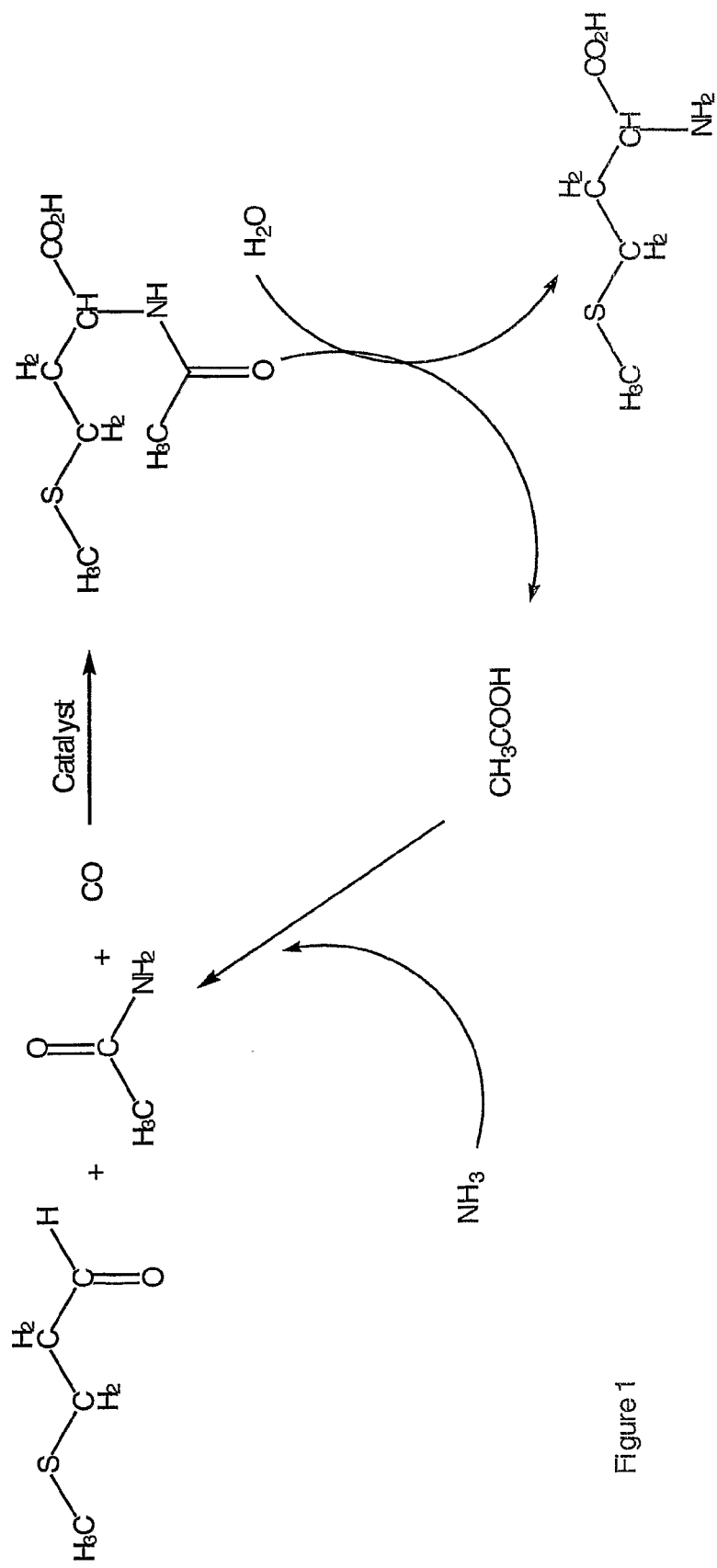

The present invention relates to a sequence for the preparation of amino acids, for example alpha-amino acids, in particular methionine, by making use of an amidocarbonylation reaction. During the process, an N-acyl amino acid is synthesised in an amidocarbonylation reaction by making use of a catalyst, and this N-acyl amino acid is then subsequently hydrolysed to the desired amino acid while the carboxylic acid thereby formed is reconverted to the corresponding carboxylic acid amide by reaction with ammonia, followed by dehydration. This carboxylic acid amide can then be re-introduced as a starting material in the initial amidocarbonylation reaction step. According to the invention, the catalyst used during the first reaction step can be recovered and recycled into the first reactor vessel. The synthesis can be conducted in a batch, semi-batch or preferably in a continuous manner.

Amino acids are important products and are correspondingly used in a variety of applications, such as human medicine, the pharmaceuticals industry as well as in the synthesis of a plurality of fine chemicals and active ingredients. In particular they are used as additives in the fodder of many livestock in enantiomerically pure form, but also in the racemic form.

Several methods are employed on an industrial scale to prepare amino acids, such as biotechnological processes, as for example fermentation processes, and hydrolysis of proteins. Chemical syntheses are also used for producing amino acids. One possibility is the Strecker reaction or its variants, such as the Bucherer-Bergs reaction. Still further, the amidocarbonylation reaction is also known to be used for preparing amino acids.

The amidocarbonylation reaction was discovered by Wakamatsu et al. in 1971 and is disclosed in the German patent application DE-A-2115985. The reaction is catalysed by various transition metal compounds and is a three component reaction between a carboxylic acid amide, an aldehyde and carbon monoxide, either in a pure form or as a mixture with hydrogen (synthesis gas) (see Scheme 1).

Scheme 1
General Reaction Scheme according to the prior art

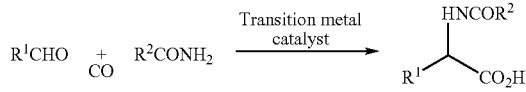

One should bear in mind that the utilisation of the amidocarbonylation reaction is to be regarded as advantageous in comparison to the conventional Strecker synthesis of amino acids or its variants since the amidocarbonylation requires carbon monoxide instead of hydrogen cyanide as one of its integral raw materials. This is of considerable advantage due to the higher price and in particular due to the high toxicity of hydrogen cyanide.

The products of the amidocarbonylation reaction are N-acyl amino acids, having the general formula:

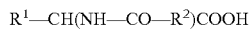

$R^1$ is: hydrogen, a linear, branched or cyclic alkyl group that has from 1 to 10 carbon atoms, especially 1 to 7, or
a linear or branched alkyl group that has from 1 to 10, especially 1 to 6 carbon atoms containing a substituent(s) amido, amino, monoalkylamino, dialkylamino, monoalkylamido, dialkylamido alkoxy, alkylthio, hydroxy, thiol, carboxylic acid or carboxylic acid alkyl ester group(s), or a 1H-imidazole-, phenyl- or 3'-indolyl-, p-hydroxyphenyl or p-alkoxyphenyl residue, whereby the said alkyl (alkoxy) group(s) has (have) 1 to 3 carbon atoms,
most preferred for $R^1$ is a linear or branched alkyl group that has from 1 to 10, especially 1 to 6 carbon atoms containing a substituent(s) amido, alkoxy, alkylthio or a phenyl or p-alkoxyphenyl residue, whereby the said alkyl group(s) has 1 to 3 carbon atoms.

$R^2$ is: hydrogen or a linear, branched or cyclic alkyl group having 1 to 10 carbon atoms, or
a linear, branched or cyclic alkyl group having 1 to 10 carbon atoms, containing a substituent(s) amido, monoalkylamido, dialkylamido hydroxy, alkyoxy, thioalkoxy group(s) or
a substituted or non-substituted aryl or benzyl group, where the substituent(s) may be a hydroxy, alkoxy, fluoro, chloro, bromo or a trialkylamino group, whereby the said alkyl group has 1 to 3 carbon atoms.

The said N-acyl amino acids are starting materials especially for the α-amino acids:

asparagine, aspartic acid, cystein, glutamine, glutamic acid, histidine, serine, threonine, tryptophan, tyrosine, most especially for alanine, glycine isoleucine, leucine, methionine, phenylalanine, valine.

Substituted hydantoins can also be prepared instead of N-acyl amino acids. In such a case, ureas are used as starting materials, as for example disclosed in the European patent application EP 1 048 656 A2.

The European patent application EP 338 330 A1 and the German patent application DE 19629717 also disclose the synthesis of various N-acyl amino acids via the amidocarbonylation reaction. DE 4415312 and DE 19545641 deal with that reaction as well, for example in the case of the industrial preparation of sarcosinates.

However, no prior art suggests a process to prepare amino acids, in particular methionine, comprising of the amidocarbonylation reaction, hydrolysis of the N-acyl amino acid formed, reuse of the catalyst and solvent from the amidocarbonylation reaction and conversion of the carboxylic acid formed during hydrolysis into a carboxylic acid amide to be reused in the first step.

With regard to this one should note that the aspect of catalyst recycling of the expensive transition metal catalyst used in the amidocarbonylation is also an important target from an economic point of view, that is avoiding the high costs involved in the acquisition of new catalyst and the disposal of spent catalyst. Recycling of the catalyst is furthermore advantageous with respect to environmental reasons due to the often high toxicity of transition metals and compounds related thereto.

A process for the recovery of cobalt carbonyl catalysts is for example described in the European patent EP 779 102 B1. According to that prior art, the active catalyst was initially oxidised after the reaction to the more stable cobalt(II) form, which was then extracted into aqueous solution, precipitated as the hydroxide and subsequently converted into a melt consisting of the hydroxide and N-acyl amino derivative which can be used for regeneration of the active catalyst under a synthesis gas atmosphere.

However, the same disadvantage as mentioned above occurs according to that prior art. For example, handling problems occur during the precipitation and drying of cobalt hydroxide. Still further, if the process were to be run in a continuous way, higher expenses would be incurred. Summing up, the processes suggested in the prior art for catalyst recovery during an amidocarbonylation reaction are not suitable for the large scale industrial synthesis of amino acids, especially methionine, due to the variety of handling problems, occurring in particular for such amino acids containing sulphur, as methionine.

There is, however, a strong need to find a way to recycle the catalyst used during the synthesis of amino acids via the amidocarbonylation. The carbonyl catalyst makes it possible to make use of carbon monoxide as a starting material, which is easier to handle and more widely available than hydrogen cyanide.

It is the object of the present invention to provide an amidocarbonylation reaction for producing amino acids providing a method of reusing and recycling the catalyst employed in the amidocarbonylation reaction to increase the efficiency of the amidocarbonylation reaction and to limit harmful emissions and environmental damage.

These objects have been solved by a process as disclosed in the patent claims. The process is also suited for producing sulphur containing amino acids, such as methionine, which might be expected to cause problems with the transition metal catalyst.

Catalyst recycling means preferably recovery and reuse of the catalyst, specifically after removal of the product from the reaction mixture, and reuse of the recovered catalyst. According to an aspect of the invention, regeneration of the catalyst from the reaction solution takes place by means of a chemical conversion into an intermediate, from which the active catalyst can be later regenerated, if necessary in a further separate step, and reused. According to the invention the catalyst is separated, recovered and subsequently reused.

In accordance with a preferred embodiment, the preparation of amino acids occurs in a continuous manner. A particularly preferred process is directed to the production of methionine.

The process according to the invention comprises the following steps:

a) Amidocarbonylation of an aldehyde with a carboxylic acid amide to give an N-acyl amino acid in the presence of a transition metal catalyst, carbon monoxide and hydrogen, b) recovery of the formed N-acyl amino acid from the reaction mixture; and c) hydrolysis of the said N-acyl amino acid in an aqueous medium to obtain the corresponding amino acid; and d) reuse of the remaining reaction mixture of step a), comprising the catalyst and solvent is after separation of said N-acyl amino acid by feeding into the amidocarbonylation step a), optionally after supplementing any lost amount of solvent and spent catalyst; and e) in a preferred case, reaction of the carboxylic acid resulting from hydrolysis with ammonia, resulting in the regeneration of the carboxylic acid amide to be used in step a).

This overall process is illustrated in FIG. 1 for the preferred case of methionine synthesis. As apparent from FIG. 1, the raw materials required are an aldehyde, for the case of methionine synthesis as demonstrated in FIG. 1, 3-(methylthio)propanal, carbon monoxide and ammonia. The ammonia is transported into the reaction in the form of acetamide used in step a) and has the function of a nitrogen carrier. Acetic acid formed during the hydrolysis step is reconverted into acetamide by reaction with ammonia and subsequent dehydration.

The hydrolysis occurring during step c) is known to the skilled person and is, for example, disclosed in the patent application WO 02/14260. Details of the regeneration reaction step of the amide can be taken from EP 919 539 A1.

In the first step the aldehyde and amide are mixed in a solvent under an inert atmosphere. The molar ratio of the aldehyde to the amide can be in the range of 1:1 to 1:5, preferably in the range of 1:1 to 1:1.5

A suitable and preferred solvent is dipolar and aprotic. Examples of these are sulphones; dimethyl sulphoxide; esters, like methyl acetate, ethyl acetate or butyl acetate; ketones, like acetone or methylisobutylketone; ethers, like tetrahydrofuran, dioxan, methyl tert-butyl ether, diisopropyl ether; amides, like dimethyl acetamide, DMF and N-methylpyrrolidine, aromatics, like toluene; nitriles, like acetonitrile and carboxylic acids.

The catalyst is preferably preformed in a separate reactor vessel from the desired cobalt precursor with carbon monoxide and hydrogen. Preferred amounts of the active catalyst are in the range of 0.1 mol % to 5 mol %, with respect to the reacting aldehyde, particularly preferred in the range of 1 to 2 mol %. A wide range of catalysts can be used, either as preformed carbonyls or formed in situ, including transition metal compounds of the following metals, Fe, Co, Ni, Ru, Rh, Pd, Ir or Pt. Preferred are compounds of Co, Pd, or Rh, especially preferred are compounds of cobalt. The presence of heteroatoms, especially sulphur, in the starting aldehyde does not negatively influence the yield of product, when cobalt is used as the metal in the catalyst.

For step a), the amidocarbonylation reaction, the solution of the amide and the aldehyde is fed into a pressure resistant vessel and the vessel is pressurised with either carbon monoxide or synthesis gas, depending on the catalyst used. Carbon monoxide is preferably applied when catalysts based on palladium are used. In the case of catalysts based on other transition metals, synthesis gas is preferred.

In the case of carbon monoxide, the preferred range of pressure is 20 to 130 bar (20,000 to 130,000 hPa) and in the case of synthesis gas the preferred range of pressures is 20 to 200 bar (20,000 to 200,000 hPa), especially preferred are 80 to 130 bar (80,000 to 130,000 hPa).

Synthesis gas with $H_2/CO$ ratios of 1:1 to 1:9 can be used, whereby the ratio of 1:8 to 1:9 is preferred. The pressure is maintained constant during the reaction.

After pressurisation is completed, the vessel is heated to a temperature in the range of 40° C. to 150° C., preferably between 60° C. and 120° C., more preferred between 60° C. and 80° C.

During the entire reaction period the reaction solution is agitated, preferably by means of stirring, enabling a maximal gas absorption into the solution.

According to a preferred embodiment of the process of the present invention, a solution of the starting amide and the catalyst are added to an organic solvent in a pressure vessel. After pressurisation to the above mentioned pressure and heating to the above mentioned temperature, the aldehyde starting material is fed into the pressure vessel by means of a pump at a constant linear or more preferably non-linear rate during the reaction. In this way the selectivity of the reaction can be increased, and the amount of unwanted side products can be diminished.

At the end of the reaction which takes between 20 minutes and 6 hours, or, if the process is run continuously, after an average residency time of the same, the reaction solution is cooled to 10° C. to 40° C., preferably 20° C. to 30° C. and depressurised to between 4 and 8 bar. The formed N-acyl amino acid precipitates from the solution and is removed by filtration.

Residues of the active catalyst are then removed by washing the N-acyl amino acid filter cake under pressure of between 4 to 6 bar with the solvent used for the reaction. These washings containing the residues of active catalyst are then recycled into the initial pressure vessel, thus avoiding the necessity for the destruction and regeneration of the active catalyst. One has to bear in mind that the active form of the catalyst is volatile and hence some quantity of catalyst might be lost during depressurisation. To avoid this effect, the gases released upon depressurisation are, after recompression, returned to the pressure reaction vessel. Catalyst dissolved in the reaction solution is recycled into the said vessel after the N-acyl amino acid is removed from the said reaction solution as described above. Some of this solution is discarded in order to prevent enrichment of the spent catalyst and has to be replaced by fresh solvent and fresh cobalt carbonyl catalyst. Experiments show an activity loss of not more than 10-15%.

After removal of the last traces of solvent by means of drying, the product N-acyl amino acid is transferred to a pressure vessel containing water. The concentration of the N-acyl amino acid in the water is in the range of 0.1 molar to 5 molar. The reaction solution is then heated to a temperature in the range of 120° C. to 180° C., preferably to between 140° C. and 160° C. Further details of such a process are known by the skilled person and are, for example, described in WO 02/14260.

After a reaction time of between 4 and 6 hours, the aqueous solution is cooled to a temperature in the range of 10° C. to 40° C. where upon the product amino acid precipitates. After filtration and drying, the desired amino acid is obtained.

In a preferred embodiment of the invention the filtrate containing the carboxylic acid formed during the hydrolysis, as well as trace amounts of the starting N-acyl amino acids, is mixed with an organic solvent immiscible with water in a counter flow extraction column. Preferred organic solvents are cyclohexanone, butanone, ethyl acetate and MIBK, particularly preferred is MIBK (methyl isobutyl ketone). The carboxylic acid is transferred into the organic layer and the aqueous solution containing impurities and the remaining starting material is returned to the hydrolysis reaction vessel. A part of the said solution is also discarded in the form of a purge, in order to prevent the build-up of unwanted side products. The organic solvent containing the carboxylic acid (in particular acetic acid) is then fed into a second counter flow extraction column, where an aqueous solution of ammonia is used as the counter flow. The reaction leads to the formation of an ammonium carboxylate in the aqueous phase which is subjected to a dehydration reaction to obtain a carboxylic acid amide. Details are known to the skilled person, or for example described in EP 919 539 A1. The organic solvent from the organic layer is separated and after drying recycled in the first extraction column.

The single processes are preferably conducted as connected processes, which is an advantage during large scale production.

The following examples are intended to illustrate the invention, without having a limiting effect.

EXAMPLES

Example 1

3.02 g acetamide, 5.36 g 3-(methylthio)propanal (97% purity) and 0.342 g of $CO_2(CO)_8$, the cobalt catalyst precursor were dissolved in 50 ml butyl acetate in a 100 ml laboratory autoclave. The reactor was pressurised to 130 bar (130,000 hPa) with 1:1 $H_2/CO$ synthesis gas and heated to 70° C. whilst stirring. The reaction was stirred for 8 hours after which the reactor vessel was cooled to room temperature and the pressure released. Analysis of the reaction mixture using HPLC gave:

| | |
|---|---|
| MMP conversion | 100% |
| Yield (N-acetyl methionine) | 92.2% |
| Selectivity (N-acetyl methionine) | 92.2% |
| Side products included approximately 1,3-bis(methylthio)propane. | 5% |

The product N-acetyl methionine was recovered by filtration of the product solution. Washing the solid with chilled ethyl acetate and drying in vacuum gave N-acetyl methionine as a white solid.

The filtrate and the wash fractions are recovered, spent catalyst amounts are supplemented and the whole is fed into step a) of the process.

Example 2

3.02 g of acetamide and 0.142 g of $CO_2(CO)_8$, the cobalt catalyst precursor, were dissolved in 20 ml of ethyl acetate in a 100 ml laboratory autoclave. The reactor was pressurised to 130 bar (130,000 hPa) with 1:1 $H_2/CO$ synthesis gas and heated to 80° C. whilst stirring. After 5 minutes a solution of 5.36 g MMP (97%) in 25 ml of ethyl acetate was slowly added using an HPLC pump at a rate of 0.42 ml/min up to 50% addition, 0.21 ml/min up to 75% addition, 0.13 ml/min up to 91% addition and 0.08 ml/min up to 100% addition. Subsequently, 5 ml of ethyl acetate were added to the reaction in order to rinse the pump and addition line. The reaction was continued for a further 2.5 hours, after which the reactor vessel was cooled to room temperature and the pressure released. Analysis of the reaction mixture using HPLC gave:

| | |
|---|---|
| MMP conversion | 96% |
| Yield (N-acetyl methionine) | 89.9% |
| Selectivity (N-acetyl methionine) | 93.6% |

Side products included <1% N-acetyl methionine ethyl ester and approximately 4% 1,3-bis(methylthio)propane.

Example 3

N-Acetyl methionine formed according to example 1 was hydrolysed to methionine and the acetic acid formed was reacted with ammonia to give acetamide.

6.40 g of N-acetyl methionine were dissolved in 50.4 g of water. The solution was transferred to a 100 ml pressure vessel and heated to 165° C. whilst stirring for 5 hours, during which the pressure remained constant at about 9 bar (9,000 hPa).

After cooling to room temperature, the solution was filtered and the recovered methionine was dried in vacuum.

| | |
|---|---|
| N-Acetyl methionine conversion | 93% |
| Yield (methionine) | 90% (60% isolated) |
| Yield (acetic acid) | 92% |

The presence of the dipeptide Met-Met as well as the diketopiperazine formed from two methionine molecules were detected by HPLC (>0.5% overall).

The filtrate containing the acetic acid formed during the hydrolysis, as well as trace amounts of the starting N-acyl amino acids, is mixed with MIBK in a counter flow extraction column.

The acetic acid is transferred into the organic layer and the aqueous solution containing impurities and the remaining unreacted starting material is returned to the hydrolysis reaction vessel. A part of the said solution is also discarded in the form of a purge, in order to prevent the build-up of unwanted side products. The organic layer containing the acetic acid is then fed into a second counter flow extraction column, where an aqueous solution of ammonia is used as the counter flow. The reaction leads to the formation of an ammonium carboxylate which is subjected to a dehydration reaction in order to obtain acetamide as described in EP 919 539 A1. The MIBK is then removed and after drying recycled in the first extractor column.

What is claimed is:

1. A process for producing an amino acid comprising the following reaction steps:
   a) amidocarbonylation reaction, wherein an aldehyde is reacted in an organic solvent with an amide and carbon monoxide and hydrogen to give an N-acyl amino acid in the presence of a transition metal carbonyl catalyst,
   b) Separating and recovering the formed N-acyl amino acid from the reaction mixture; and
   c) hydrolysis of the recovered N-acyl amino acid in an aqueous medium to obtain the corresponding amino acid;
   c1) recovery and recycling the catalyst; and,
   d) reuse of the reaction mixture of step a) comprising the catalyst and solvent after separation of the N-acyl amino acid by feeding into the amidocarbonylation step a) optionally after supplementing lost solvent and spent catalyst.

2. The process according to claim 1, wherein said N-acyl amino acids have the general formula

$R^1$ is: hydrogen, a linear, branched or cyclic alkyl group that has from 1 to 10 carbon atoms, or a linear or branched alkyl group that has from 1 to 10 carbon atoms containing a substituent(s) amido, amino, monoalkylamino, dialkylamino, monoalkylamido, dialkylamido alkoxy, alkylthio, hydroxy, thiol, carboxylic acid or carboxylic acid alkyl ester group(s), or a 1H-imidazole-, phenyl- or 3'-indolyl-, p-hydroxyphenyl or p-alkoxyphenyl residue, whereby said substituent(s) groups comprise alkyl (alkoxy) group(s) with 1 to 3 carbon atoms, R2 is: hydrogen or a linear, branched or cyclic alkyl group having 1 to 10 carbon atoms, or a linear, branched or cyclic alkyl group having 1 to 10 carbon atoms, containing a substituent(s) amido, monoalkylamido, dialkylamido hydroxy, alkyoxy, thioalkoxy group(s) or a substituted or non-substituted aryl or benzyl group, where the substituent(s) may be a hydroxy, alkoxy, fluoro, chloro, bromo or a trialkylamino group, whereby the alkyl group on said substituent(s) has 1 to 3 carbon atoms.

3. The process according to claim 1, comprising the reaction step to regenerate the amide used in step a), whereby
   a) after separation of the amino acid the carboxylic acid formed by hydrolysis is extracted and brought into contact with aqueous ammonia,
   b) formed ammonium carboxylate is separated, and
   c) said carboxylate is subjected to a dehydration reaction for obtaining carboxylic acid amide, and
   d) said carboxylic acid amide is fed to the amidocarbonylation process.

4. The process according to claim 1, wherein methionine is produced from 3-(methylthio)propanal by amidocarbonylation.

5. The process according to according to claim 1, wherein the single processes are connected to form a circular system and are conducted in a continuous manner.

6. The process according to claim 2, comprising the reaction step to regenerate the amide used in step a), whereby
   a) after separation of the amino acid the carboxylic acid formed by hydrolysis is extracted and brought into contact with aqueous ammonia,
   b) formed ammonium carboxylate is separated, and
   c) said carboxylate is subjected to a dehydration reaction for obtaining carboxylic acid amide, and
   d) said carboxylic acid amide is fed to the amidocarbonylation process.

7. The process according to claim 2, wherein methionine is produced from 3-(methylthio)propanal by amidocarbonylation.

8. The process according to claim 3, wherein methionine is produced from 3-(methylthio)propanal by amidocarbonylation.

9. The process according to claim 2, wherein the single processes are connected to form a circular system and are conducted in a continuous manner.

10. The process according to claim 3, wherein the single processes are connected to form a circular system and are conducted in a continuous manner.

11. The process according to claim 2, wherein said linear, branched or cyclic alkyl group is comprised of from 1 to 7 carbon atoms.

12. The process according to claim 1, wherein said recovered catalyst is combined with a newly-provided catalyst in step d).

* * * * *

UNITED STATES PATENT AND TRADEMARK OFFICE
CERTIFICATE OF CORRECTION

PATENT NO. : 7,572,937 B2  
APPLICATION NO. : 11/570319  
DATED : August 11, 2009  
INVENTOR(S) : Hateley et al.

Page 1 of 1

It is certified that error appears in the above-identified patent and that said Letters Patent is hereby corrected as shown below:

On title page, item (75) Inventors:  
Replace "Thomas Hauhlner"  
with -- Thomas Häussner --

Signed and Sealed this

First Day of December, 2009

David J. Kappos  
*Director of the United States Patent and Trademark Office*